United States Patent [19]

Seely

[11] Patent Number: 5,747,639
[45] Date of Patent: May 5, 1998

[54] USE OF HYDROPHOBIC INTERACTION CHROMATOGRAPHY TO PURIFY POLYETHYLENE GLYCOLS

[75] Inventor: James Ervin Seely, Louisville, Colo.

[73] Assignee: Amgen Boulder Inc., Boulder, Colo.

[21] Appl. No.: 611,918

[22] Filed: Mar. 6, 1996

[51] Int. Cl.[6] .................................................. B01D 15/06
[52] U.S. Cl. ...................... 528/421; 210/198.2; 210/656
[58] Field of Search ............................... 210/656, 198.2; 528/421

[56] References Cited

U.S. PATENT DOCUMENTS

| | | | |
|---|---|---|---|
| 5,094,960 | 3/1992 | Bonomo | 436/178 |
| 5,349,052 | 9/1994 | Delgado et al. | |
| 5,476,653 | 12/1995 | Pitt et al. | 424/78.3 |

FOREIGN PATENT DOCUMENTS

95/13312  5/1995  WIPO.

OTHER PUBLICATIONS

Barka, G & Hoffmann, P, "Simultaneous Separation of Oligomeric and Polymeric Ethylene Glycols (Degree of Polymerization 1–110) Using Reversed–Phase High–Performance Liquid Chromatography" *Journal of Chromatography*, 389: 273–278 (1987).

Lai et al, "Separations of Water Soluble Polyehtylene Glycol Oligomers on Phenyl–Bonded Phase Using Low Wavelength UV Detection at 190 nm", *Journal of High Resolution Chromatography & Chrom. Communications*, 7: 494–496 (1984).

Meyer, "Analysis of Polyethylene Glycos with Respect to Their Oligomer Distribution by High–Performance Liquid Chromatography", *Journal of Chromatography*, 645: 135–139 (1993).

Murphy et al, "High–Performance Liquid Chromatographic Analysis of Polyethylene Glycols", *Journal of Chromatography*, 211: 160–165 (1981).

Trathnigg et al, "Analysis of Polyethers by Isocratic HPL with Universal Detectors. I. Optimization of Chromatographic Conditions", *Journal of Liquid Chromatography*, 16(12): 2439–2452 (1992).

Van Der Wal, S and Snyder, L, "Photometric Detection at 185 nm for High–Performance Liquid Chromatography with Either Isocratic or Gradient Elution", *Journal of Chromatography*, 255: 463–474 (1983).

*Primary Examiner*—Peter F. Kulkosky
*Attorney, Agent, or Firm*—Craig Crandall; Steven Odre; Ron Levy

[57] ABSTRACT

The present invention relates to a process for purifying polyethylene glycols (PEGs) which utilizes hydrophobic interaction chromatography (HIC) to separate the PEGs based on their size and on their end-group functionality. The purified PEGs can be used to modify biologically active molecules and improve overall production of such molecules.

16 Claims, 11 Drawing Sheets

USE OF HYDROPHOBIC INTERACTION CHROMATOGRAPHY TO PURIFY POLYETHYLENE GLYCOLS

FIELD OF THE INVENTION

The invention relates to an efficient process for purifying polyethylene glycols (PEGS) which utilizes hydrophobic interaction chromatography (HIC) to separate the PEGs based on size and end-group functionality. More particularly, the invention is directed to a process for purifying 20K polyethylene glycol bis-vinylsulfone ("20K PEGbv") which utilizes a Butyl or Phenyl HIC resin to separate high molecular weight PEG impurities and PEG mono-vinylsulfone from the 20K PEGbv. The process does not require the addition of organic solvents and the purified 20K PEGbv can be used to modify certain biologically active proteins.

BACKGROUND OF THE INVENTION

Polyethylene glycols ("PEGs") are long chain, linear synthetic polymers composed of ethylene oxide units. The ethylene oxide units can vary such that PEG compounds can be obtained with molecular weights ranging from approximately 200–100,000. PEG typically is colorless, odorless, soluble in water, stable to heat, does not hydrolyze or deteriorate, and is non-toxic. As such, PEGs have been extensively studied for use in pharmaceuticals, on artificial implants, and other applications where biocompatibility is of importance.

The attachment of PEG to proteins ("PEGylation") has been shown to: (1) increase the plasma half-life of the proteins, see e.g., U.S. Pat. No. 5,349,052, Delgado et al., issued Sep. 20, 1994; (2) alter the biochemical and physical properties of the protein, including increasing solubility, Chen et al., Biocem. Biophys. Acta. 660: 293–298 (1988), and improving protection against proteolysis, Sada, et al., J. Fermentation Bioengineering 71:137–139 (1991); and (3) reduce antigenicity, Davis et al., "Biomedical Polymers. Polymeric Materials and Pharmaceuticals for Biomedical Use", (Eds. Goldberg & Nakajima) pp 441–452, Academic Press, N.Y. (1980).

Various derivatives of PEG have been proposed that have an active moiety for permitting PEG to be attached to proteins. The vast majority of PEGylating reagents react with free primary amino groups of the polypeptide. Most of these free amines are the $\epsilon$-$NH_2$ group of lysine amino acid residues; and, because typical proteins possess a large number of lysine residues, random attachment of multiple PEG molecules often occurs, which can lead to loss of protein activity.

Published PCT Publication No. WO 95/13312 describes, inter alia, water soluble sulfone-activiated PEGs which are highly selective for coupling with thiol moieties instead of amino moieties on molecules and on surfaces. These PEG derivatives are stable against hydrolysis for extended periods in aqueous environments at pHs of about 11 or less, and can form linkages with molecules to form conjugates which are also hydrolytically stable. The linkage by which the PEGs and the biologically active molecule are coupled includes a sulfone moiety coupled to a thiol moiety and has the structure PEG-$SO_2$-$CH_2$-$CH_2$-S-W, where W represents the biologically active molecule, and wherein the sulfone moiety is vinyl sulfone or an active ethyl sulfone.

One example of a biologically active molecule which can be modified by such sulfone-activated polymers is TNF binding protein ("TNFbp") (also referred to as TNF inhibitor). TNFbp is of therapeutic interest in the treatment of disease states such as rheumatoid arthritis and septic shock. Several forms of native TNFbp, e.g., 30 kDa and 40 kDa TNFbp have been described in detail; see e.g., published European Patent Application No. 90 113 673.9, incorporated herein by reference. Furthermore, various TNFbp muteins, e.g., c105 30 kDa TNFbp mutein (the asparagine residue at position 105 of the native human protein is changed to cysteine) have been prepared and described; see published PCT Publication No. WO 92/16221, incorporated herein by reference.

PCT Publication No. WO 92/16221 further describes TNFbp forms represented by the formula $R_1$-X-$R_2$ (referred to as a "dumbbell" compound), wherein $R_1$ and $R_2$ are biologically active TNFbp groups and X is a non-peptidic polymeric spacer with at least one Michael acceptor group, e.g. a sulfone-activated PEG. One particular compound, referred to as c105 TNFbp mutein dumbbell, is a homo-dumbbell compound wherein $R_1$ and $R_2$ is a c105 30 kDa TNFbp mutein, X is 20K polyethylene glycol bis-vinylsulfone (20K PEGbv), and wherein $R_1$ and $R_2$ are attached site-specifically at the cysteine 105 residue to the PEGbv. This c105 TNFbp mutein dumbbell was reported to be many times more active than the unPEGylated native 30 kDa TNFbp, unPEGylated c105 30 kDa TNFbp mutein or the PEGylated 30 kDa TNFbp "monobell" ($R_1$-X).

A problem commonly encountered by those skilled in the art when producing compounds such as the c105 TNFbp mutein dumbbell is that the procedures used to synthesize the 20K PEGbv, or other polymer, have several drawbacks, depending on the synthesis procedure used. One particularly problematic drawback is that the resultant 20K PEGbv will often contain high molecular weight PEG impurities and PEG mono-vinylsulfone. These impurities can then adversely affect the overall yield and purity of the desired dumbbell compound. The need exists, therefore, for methods which would further purify the PEGbv, or other polymers, and thereby enhance the overall purity and yield of the desired dumbbell compound, and make utilization of such compounds as therapeutic agents more commercially practicable.

A number of groups have reported on the use of reversed-phase high performance liquid chromatography (rpHPLC) to separate low- and medium-molecular weight (<5K) PEGs on the basis of size; see e.g., Murphy et al., J. Chromat., 211: 160–165 (1981); Lai et al., J. High Res. Chrom. & Chrom. Comm., 7:494–496 (1984); Barka & Hoffman, J. Chromat., 389:273–278 (1987). These techniques, while relatively effective, suffer from their use of expensive resins and organic solvents. Also, these methods are analytical rather than preparative procedures. There have been no reports of successful separation of larger molecular weight PEGs using HPLC. Medium- and high-molecular-weight (1K–40K) PEGs have been analyzed by size exclusion chromatography on a variety of derivatized silica supports; Engelhardt & Mathes, J. Chromat., 185:305 (1979).

Hydrophobic interaction chromatography (HIC) has achieved acceptance as an analytical and preparative purification method for biomolecules. The chemical principles underlying HIC are similar to those involved in salt precipitation, and related to those associated with reversed phase liquid chromatography (RPLC), in that all operate on the basis of hydrophobicity. HIC is characterized by adsorption of molecules to a weakly hydrophobic surface at high salt concentrations, followed by elution with a decreasing salt gradient. Thus, HIC combines the non-denaturing characteristics of salt precipitation and the precision of chromatography to yield excellent activity recoveries. Moreover, because HIC operates at lower binding energy, it does not require the use of expensive organic solvents in the mobile phase.

To date, there have been no reports concerning the use of HIC resins to separate PEGs, especially high molecular weight PEGs.

SUMMARY OF THE INVENTION

It is therefore an object of the present invention to provide a process for purifying non-peptidic polymers, in particular, sulfone-activated polymers, which utilizes HIC to separate the polymers based on size and end-group functionality. Importantly, purifications carried out in this manner do not require the addition of organic solvents. More importantly, the purified polymers can be used to modify various proteins and provide biologically-active conjugates with dramatically improved purity and overall yield as compared to conjugates formed with non-purified polymers.

Polymers contemplated for use include water soluble polymers such as polyethylene glycol ("PEG") and related hydrophilic polymers. The biologically-active molecule can be a synthetic, a naturally occurring, or a modified naturally occurring molecule.

In one aspect of the invention, a PEG or other non-peptidic polymer linker, having a molecular weight ranging from 5 kDa to 100 kDa, is applied to, and eluted from, an HIC resin using conventional chromatographic methods. In a preferred embodiment, the linker is eluted from the resin using a reverse linear salt gradient, such that the various linker forms are separated based on size and/or end-group functionality. Preferably, the linker is a sulfone-activated PEG linker and the HIC comprises a Butyl or Phenyl HIC resin. In a particularly preferred embodiment, the invention is directed to a process for purifying 20K polyethylene glycol bis-vinylsulfone ("20K PEGbv") utilizing a Toyopearl® Butyl-650M HIC resin to separate high molecular weight PEG impurities and PEG mono-vinylsulfone from the 20K PEGbv.

In yet another aspect of the invention, an HIC-purified, non-peptidic polymer linker is reacted with a biologically-active molecule in order to provide a dumbbell compound having improved overall purity and yield as compared to previously described compounds containing the same molecule. Preferably, the HIC-purified polymer linker is a sulfone-activated PEG, and the biologically-active molecule is selected from the group consisting of TNF inhibitors, interleukin-1 receptor antagonists ("IL-1ra's"), exon six peptide of platelet-derived growth factor ("PDGF"), and interleukin-2 ("IL-2") inhibitors and receptors ("IL-2r"). In a particularly preferred embodiment, the HIC-purified polymer linker is 20K PEGbv, the biologically-active molecule is TNFbp.

Pharmaceutical compositions containing the compounds of the present invention are also included within the scope of the invention.

DETAILED DESCRIPTION

Figure 1:
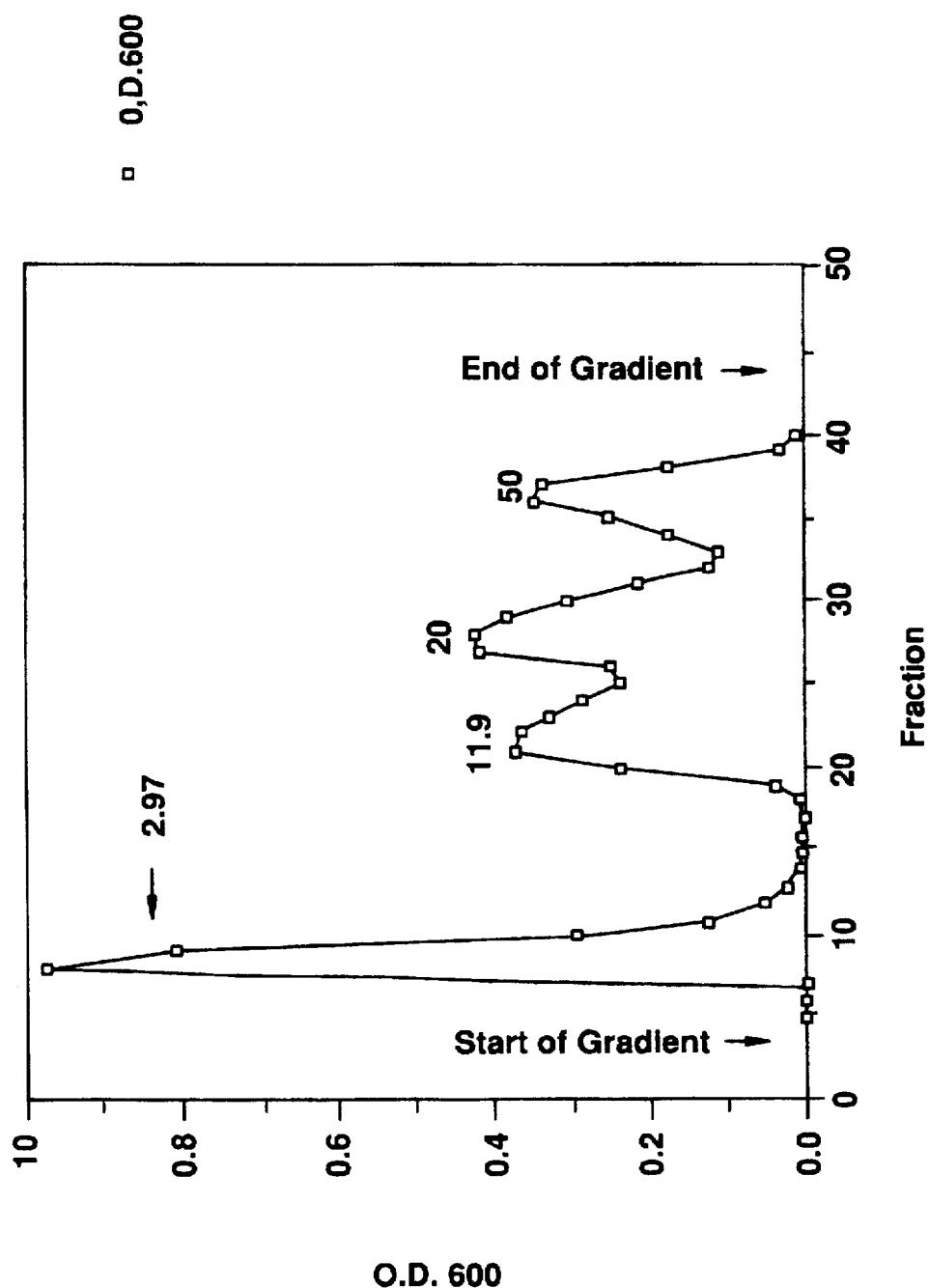
FIG. 1 depicts the elution profile of various PEG diols from a ToyoPearl® Butyl 650M HIC column. PEG-containing fractions were detected with Nessler's reagent and the molecular weights confirmed by SEC HPLC as described in Example 3.

The processes by which hydrophobic interaction chromatography can be used to purify polyethylene glycols, and other polymers, are described in more detail in the discussion below and are illustrated by the examples provided below. The examples show various aspects of the invention and include results of the use of butyl and/or phenyl HIC resins to separate high molecular weight PEG impurities from a sulfone-activated PEG, 20K PEGbv. The results were surprising in that HIC also separated PEG mono-vinylsulfone from the 20K PEGbv, and the resultant purified 20K PEGbv, when used to PEGylate TNPbp, provided a biologically active conjugate having dramatically improved overall yield and purity as compared to conjugates prepared using non-HIC-purified 20K PEGbv.

HIC contemplated for use in the present invention utilizes polymeric resins wherein a hydrophobic pendant group (e.g. octyl, butyl, phenyl or ether) is located on the surface of a hydrophilic vinyl copolymer backbone resin, including, but not limited to, a methacrylic, agarose, or vinylic backbone. A silica based backbone could also be used. Preferred HIC columns will have either a butyl or phenyl ligand on a methacrylic backbone.

The term "PEG" as used herein means any of several condensation polymers of ethylene glycol. PEG is also known as polyoxyethylene, polyethylene oxide, polyglycol, and polyether glycol. PEG can also be prepared as copolymers of ethylene oxide and many other monomers. The end groups of the PEG can be derivatized in a variety of ways to include vinylsulfone moieties, aldehyde moieties, methoxy groups, or other types of reactive or nonreactive end-groups.

The polymeric derivatives of the present invention have active sulfone moieties. "Active sulfone" means a sulfone group to which a two carbon group is bonded having a reactive site for thiol-specific coupling on the second carbon from the sulfone group at about pH or less. Examples of active sulfones include, but are not limited to, vinyl sulfone and activated ethyl sulfone. The sulfone-activated polymer can be further substituted as long as the thiol-specific reactivity at the second carbon is maintained at about pH 9 or less. The sulfone-activated polymers can be synthesized as described in co-pending U.S. patent application Ser. No. 08/259,413, specifically incorporated herein by reference, or prepared as described in Example 1 below.

The activated polymeric derivatives of the present invention can have more than one reactive group. The derivatives can be monofunctional, bifunctional, or multifunctional. The reactive groups may be the same (homofunctional) or different (heterofunctional) as long as there is at least one active sulfone moiety. Two particularly useful homobifunctional derivatives are PEG-bis-chlorosulfone and PEG-bis-vinyl sulfone.

A general method for purifying the non-peptidic polymers includes the following steps:

(1) synthesize the non-peptidic polymer linker;

(2) apply the non-peptidic polymer linker to an HIC resin;

(3) isolate the desired polymer linker form by eluting the polymer from the HIC resin using conditions, e.g., reverse linear salt gradient, which allow for separation of the various linker forms based on size and/or end-group functionality.

Alternatively, the HIC purification step could be incorporated into the polymer linker synthesis procedure.

Biologically-active molecules include, but are not limited to, pharmaceuticals, vitamins, nutrients, nucleic acids, amino acids, polypeptides, enzyme co-factors, steroids, carbohydrates, organic species such as heparin, metal containing agents, receptor agonists, receptor antagonists, binding proteins, receptors or portions of receptors, extracellular matrix proteins, cell surface molecules, antigens, haptens, and chelating agents.

"Polypeptides" and "proteins" are used herein synonymously and mean any compound that is substantially proteinaceous in nature. Also included within the scope of the invention are truncated forms of the native polypeptide or polypeptides which are modified to contain an amino acid residue in a position where one was not present in the native protein before such modification ("mutein"). Many polypeptides useful in the present invention are set forth in published PCT Publication No. WO 92/16221, specifically incorporated herein by reference.

In general, TNFbp useful in the present invention has the sequence of human TNFbp, or closely related analogues thereof. One TNFbp, referred to as 30 kDa TNFbp, or TNFbp I, is the extracellular portion of the p55 TNF receptor. In vivo, the extracellular portion of the receptor is shed and circulates in the bloodstream as a 30 kDa glycosylated protein which binds TNF. The purification and amino acid and nucleic acid sequences of this TNFbp are set forth in published European Patent Application No. 90 113 673.9, which is incorporated herein by reference. This reference also teaches the recombinant production of glycosylated and deglycosylated forms of 30 kDa TNFbp. Although the actual molecular weight of the deglycosylated form of this inhibitor is approximately 18 kDa, the term "30 kDa TNF inhibitor" includes the glycosylated and deglycosylated forms.

The purification and amino acid and nucleic acid sequences of another TNF inhibitor, called 40 kDa TNFbp or TNFbp-II, is also set forth in European Patent Application No. 90 113 673.9. This inhibitor, in its naturally-occurring form, is the glycosylated extracellular portion of the p75 or p85 TiNF receptor. Although the molecular weight of the deglycosylated form is not 40 kDa, both the glycosylated and deglycosylated forms of this TNFbp are referred to as "40 kDa TNF inhibitor.

Furthermore, PCT Publication No. WO 92/16221, incorporated herein by reference, describes the preparation of various TNFbp muteins, e.g., c105 30 kDa TNFbp mutein (the asparagine residue at position 105 of the native human protein is changed to cysteine).

While the procedures described in the published references above are the preferred methods for producing recombinant TNFbp forms, modifications and changes could be made to that process as known in the art.

As stated above, the HIC-purified, sulfone-activated polymers can be reacted with a thiol-containing biologically active molecule to provide biologically active conjugates. The linkage between the thiol reactive group and the sulfone-activated polymer is a covalent bond, and the general method for preparing such conjugates includes the following steps:

(1) select the desired biologically-active molecule;

(2) synthesize the desired non-peptidic polymer linker;

(3) purify the polymer using HIC chromatography;

(4) react the HIC-purified, activated polymer with the molecule;

(5) isolate the reaction product using chromatographic techniques well known in the art. (6) determine the biological activity of the conjugate formed using the relevant bioassay.

The conjugates of the present invention can be used for a variety of purposes including, but not limited to, in-vitro diagnostic assays and the preparation of pharmaceutical compositions. Conjugates containing TNFbp can be used to treat TNF-mediated diseases such as adult respiratory distress syndrome, pulmonmary fibrosis, arthritis, septic shock, inflammatory bowel disease, multiple sclerosis, graft rejection and hemorrhagic trauma.

Pharmaceutical compositions containing many of the conjugates or compounds (collectively, the "conjugates") of the present invention can be prepared. These conjugates can be in a pharmaceutically-acceptable carrier to form the pharmaceutical compositions of the present invention. The term "pharmaceutically acceptable carrier" as used herein means a non-toxic, generally inert vehicle for the active ingredient, which does not adversely affect the ingredient or the patient to whom the composition is administered. Suitable vehicles or carriers can be found in standard pharmaceutical texts, for example, in "Remington's Pharmaceutical Sciences", 16th Ed., Mack Publishing Co., Easton, Pa. (1980), incorporated herein by reference. Such carriers include, for example, aqueous solutions such as bicarbonate buffers, phosphate buffers, Ringer's solution and physiological saline. In addition, the carrier can contain other pharmaceutically-acceptable excipients for modifying or maintaining the pH, osmolarity, viscosity, clarity, color, sterility, stability, rate of dissolution, or odor of the formulation.

Although the invention has been described and illustrated with respect to certain purification processes which utilize hydrophobic interaction chromatography for purifying non-peptidic polymers based on size and end-group functionality, it will be apparent to one of ordinary skill that additional embodiments may exist without departing from the scope of the invention.

The following examples will illustrate in more detail the various aspects of the present invention.

EXAMPLE 1

This example describes the preparation of the 20K PEGbv used in the present invention. The 20K PEGbv was prepared as set forth in PCT/US95/07555, specifically incorporated herein by reference. Alternatively, the 20K PEGbv can be prepared using the "One-step" synthesis procedure discussed below.

"One-step" Synthesis of 20K PEGbv

Polyethylene glycol (PEG-DIOL) was purchased from Shearwater Polymers Inc. Divinylsulfone, 1M potassium t-butoxide (in tetrahydrofuran (THF)), toluene (anhydrous, sure seal), di-i-propyl ether (99+%, inhibited with 25 ppm butylated hydroxy toluene (BHT)), and tetrahydrofuran (anhydrous containing 0.025% BHT as inhibitor, sure seal) were obtained from Aldrich Chemical Company. Dichloromethane (Omni solvent) and diethyl ether (EM) were bought from VWR Scientific Company. Anhydrous sodium sulfate powder was purchased from J. T. Baker.

A 22 L four-necked (one 45/50 and three 24/40 joints) round bottom flask was fitted with a thermometer, condenser, a rubber septa, and a variable speed mechanical stirrer and immersed in a water bath containing an immersion water heater. The flask was kept under positive argon pressure. The condenser was connected to a two-neck round-bottom flask through which vacuum line was attached. Polyethylene glycol (20K, 300 g, 15 mmole) was weighed and transferred to the 22 L flask through a funnel and three liters of anhydrous toluene was cannulated while the mixture was stirring. The water bath temperature was set at 45° C. and the stirring continued until the solution became clear (~1 h). The solvent was evaporated under vacuum (~60 mm of Hg) to dryness. The solid residue was dissolved in nine liters of anhydrous tetrahydrofuran (added via cannula). The water bath temperature was set at 25° C. Stirring was continued until the temperature of the solution became 25° C. Divinylsulfone (6 ml, 59.97 mmole) was added from a syringe over 15 min. The mixture was stirred (75 rpm) for 10 min. Potassium t-butoxide (1M in THF, 3 ml, 3 mmole) was added from a dropping funnel over a period of 25 min. After the addition of the base, the reaction mixture was stirred at 25° C. for six hours. The water bath was then heated to 40° C. and the THF was evaporated (350 mm of Hg). One liter of 1:1 mixture of dichloromethane and tetrahydrofuran was added to the solid residue and stirred until a clear solution was formed. The solution was cooled to 25° C. and chilled (-20° C.). Di-i-propyl ether (1×5 liter) was added to the solution from a dropping funnel while the stirring was continued. The condenser connection was removed from the flask. A pressure filter funnel was connected to the flask through a flex needle and the precipitate transferred via the flex needle and filtered through the filter funnel (1 L, 70–100µ) under vacuum. The precipitate was split into two portions, transferred into 2 L erlenmeyers and left stirring (magnetic stirrer) with one liter (each) of i-propyl ether for three hours. The precipitate was filtered (2 L, 70–100µ), washed with 800 ml of diethyl ether and dried under vacuum (5 mm of Hg) in a desiccator for 72 h. The yield was determined to be 278.6 g (91.6% recovery based on the weight of polyethylene glycol).

The product was transferred to an erlenmeyer flask (2 L) and a liter of dichloromethane (Omni Solvent) added. After all the product had dissolved the solution (in syrup form) was transferred to a 5 L drop bottom flask fitted with a mechanical stirrer. The erlenmeyer flask was rinsed with another 500 ml of dichloromethane and the solution added to the drop bottom flask. The solution was then stirred for 5 min (65 rpm). Saturated sodium chloride (1 L) was added and stirred for 5 min (75 rpm). The mixture was allowed to settle till the two layers became distinct. The organic layer was withdrawn and kept in a separate container. This process was repeated three times and all the organic layers were combined.

The solution was then split into two portions (3 L each) and transferred into two erlenmeyers (4 L) and stirred for 16 hours with 500 g of anhydrous sodium sulfate powder (J. T. Baker), at room temperature, using a magnetic stirrer (during this process the flask was completely covered with aluminum foil). The solution was filtered through a filter funnel (2 L, 70–100µ) and the filtrate transferred to a 22 L four-necked flask, the flask having been placed in a water bath (40° C.). The solvent was evaporated under vacuum (285–360 mbar) and the residue (very viscous liquid) re-dissolved in a 1:1 mixture of dichloromethane and THF (1 L). The solution was then precipitated, filtered, and dried as previously described. The yield was determined to be 221.0 g (72.67% recovery based on the weight of polyethylene glycol).

EXAMPLE 2

This example describes a series of loading and elution experiments designed to test the capability of Butyl, Phenyl and Ether HIC resins to bind 20K PEGbv.

Assays Utilized

1. PEG Assay

PEG-containing fractions were detected with Nessler's reagent (Sigma/Aldrich). Typically, 0.01 mL of Nessler's reagent is added to a 0.25 mL aliquot of a column fraction in a glass test-tube. PEG-containing fractions will form a milky precipitate upon addition of the Nessler's reagent.

2. Quantitative PEG Analysis

Nessler's reagent (1.5 mL) is added to a glass test-tube, followed by 18.75 microliters of the sample to be tested. The test-tubes are vortexed, allowed to stand for 10–15 minutes, and turbidity read at 600 nm vs. a blank containing Nessler's reagent alone (Beckman DU 70 Spectrophotometer). PEG is then quantitated from a standard curve made up of 1.5, 1.0, 0.75, 0.50 and 0.25 mg/mL PEG standard.

Experimental Runs 5 mL prepacked ToyoPearl® Butyl, Phenyl and Ether 650C HIC columns were used. Columns were loaded with 10 mg (2 mg/mL bed volume) 20K PEGbv in various concentrations of NaCl or sodium sulfate, and then eluted with water by gravity. All experiments were conducted at room temperature, and 0.5–1.0 mL fractions were collected by hand into 13×100 mM glass test-tubes. PEG was determined by the Nessler's assay.

Table 1 sets forth the salt concentrations necessary for complete binding (i.e., no PEGbv detectable in the flowthrough) of 20K PEGbv to the various HIC resins.

9

TABLE 1

| Resin | NaCL [ ] | Sodium Sulfate [ ] |
| --- | --- | --- |
| Phenyl 650C. | 2.25 M | 0.35 M |
| Butyl 650C. | 1.75 M | 0.25 M |
| Ether 650C. | >>2 M | >>0.5 M |

As indicated in Table 1, the Butyl 650C HIC resin has a slightly greater affinity for PEG than does the Phenyl 650C HIC resin, while the Ether 650C HIC resin did not bind any PEG when loaded at either 2M NaCl or 0.5M sodium sulfate.

EXAMPLE 3

This example describes an experiment designed to test the capability of a Butyl HIC resin to separate various PEG diols based on size. PEG-containing fractions were determined using the PEG assay described above and the molecular weight of the PEGs were confirmed by SEC HPLC.

Assays Utilized

1. Size-exclusion Chromatoaraphy (SEC) HPLC Assay

Size-exclusion chromatography of the HIC-purified PEG fractions was performed using a Toso-Haas G3000$_{pwxl}$ column (Synchrom, Inc., Linden N.J.). A 100–200 µl sample at 0.5–1.0 mg/mL is injected. The column is run at room temperature and the equilibrated in 10 mM sodium phosphate buffer, 150 mM NaCl, 0.004% sodium dodecyl sulfate (SDS), pH 6.5. The PEG is eluted from the column using a buffer containing 10 mM sodium phosphate, 150 mM NaCl, and 0.004% SDS, pH 6.5. In some experiments, a Bio-Rad Refractive Index detector was used to monitor the PEG elution. In other experiments, the PEG was first derivatized with o-thiobenzoic acid so that the eluate could be monitored by UV absorbance at 254 nm.

Experimental Runs

A ToyoPearl® Butyl 650M HIC column (1.5×11 cm) was loaded with a total of 3 mg PEG diol per mL column bed volume. The column was equilibrated in 4M NaCl. The load volume was 9.7 mL and contained 2.97 kDa, 11.9 kDa, 20 kDa and 50 kDa PEG diol, each at 1.5 mg/mL (the 2.97 kDa and 11.9 kDa PEG diols were purchased from Polymer Laboratories and the 20 kDa and 50 kDa PEG diols were purchased from Shearwater Polymers). After loading, the column was washed with 2 column volumes of 4M NaCl, and eluted with a linear 15 column volume gradient from 3M to 1M NaCl. The flow rate for load, wash and elution steps was 2.5 mL/min. Three minute fractions were collected and fractions were analyzed for PEG. The elution profile is shown in FIG. 1. The molecular weights of the four peaks were confirmed by size-exclusion HPLC chromatography and are shown as indicated.

To complete these initial experiments, the PEGbv that eluted in the 2M NaCl flow-through and water eluate of the Phenyl 650C column described in Example 2 was analyzed in the SEC HPLC assay. The SEC HPLC data revealed that the material in the 2M NaCl flow-through was enriched for 20K PEGbv, whereas the material in the water eluate contained predominantly high molecular weight PEGbv. This data confirms that HIC; in particular, Phenyl and/or Butyl HIC, can be used to separate PEG diols and 20K PEGbv on the basis of size.

EXAMPLE 4

This example describes a series of HIC experiments wherein various 20K PEGbv loading conditions were tested and wherein various linear NaCl gradients were used to elute the PEGbv from the Butyl or Phenyl HIC resins. All experiments were run at room temperature and generally carried out as described in Example 2.

Run 1

Figure 2:
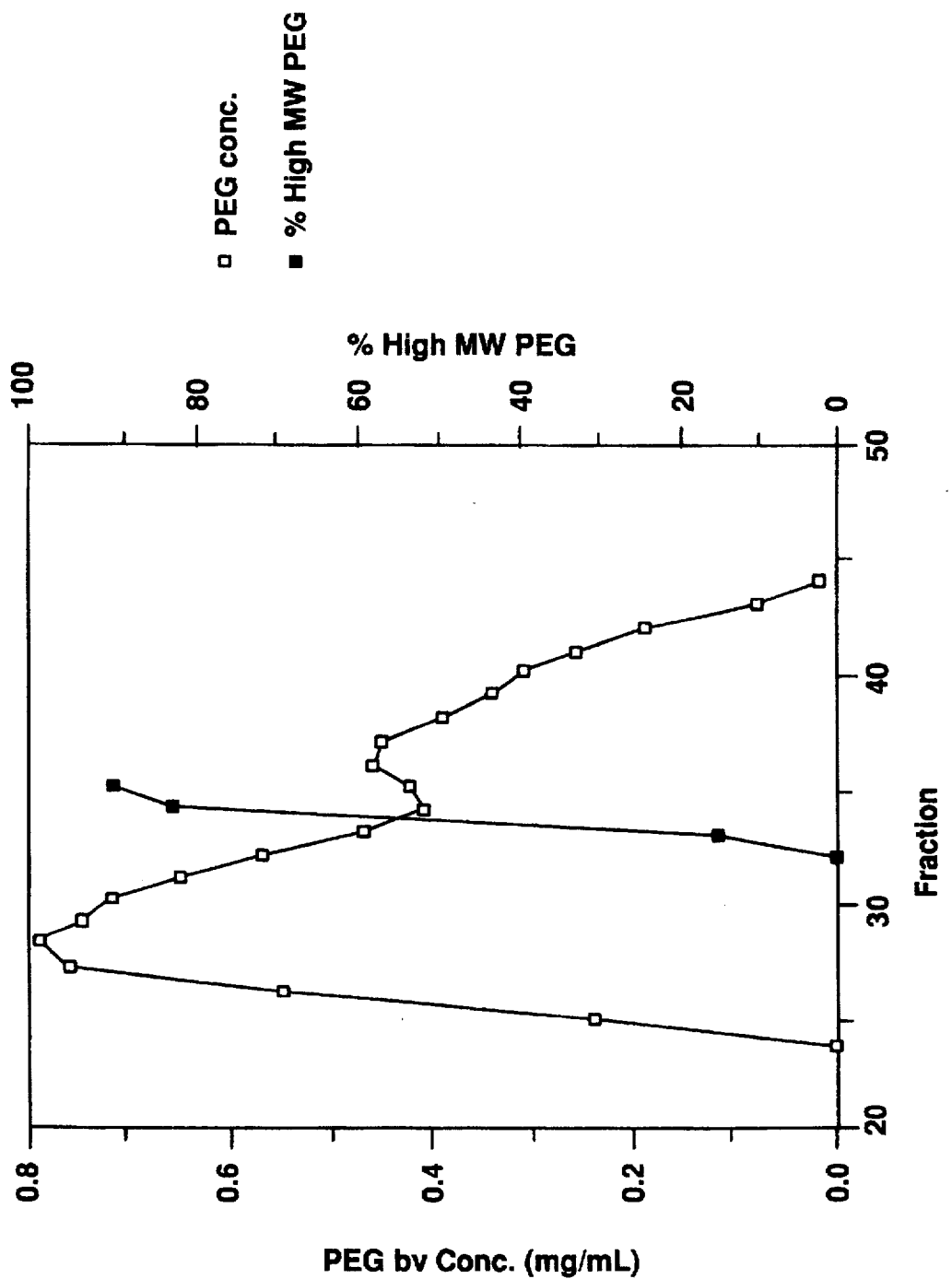
FIG. 2 depicts the elution profile of 20K PEGbv and high molecular weight PEGbv from a ToyoPearl® Phenyl 650S HIC column (2 mg/mL bed volume loading). PEGbv concentration was determined by Nessler's reagent and the % molecular weight impurity was determined by SEC HPLC as described in Example 3.

Run 1 used a ToyoPearl® Phenyl 650S HIC column (1.5×6.5 cm). The 650S resin differs from the 650C resin in that the particle size is 20–50 microns rather than 50–150 microns. The column was equilibrated in 3M NaCl, and 2 mg/mL bed volume PEGbv was loaded onto the column. The PEGbv was eluted using a 10 column volume linear NaCl gradient (3M NaCl to 0M NaCl) and a flow-rate of 1.5 mL/minute. 2 minute fractions were collected and the elution profile is depicted in FIG. 2. The % yield of 20K PEGbv was then determined using the assay described in Example 3 (see Table 2).

Run 2

Figure 3:
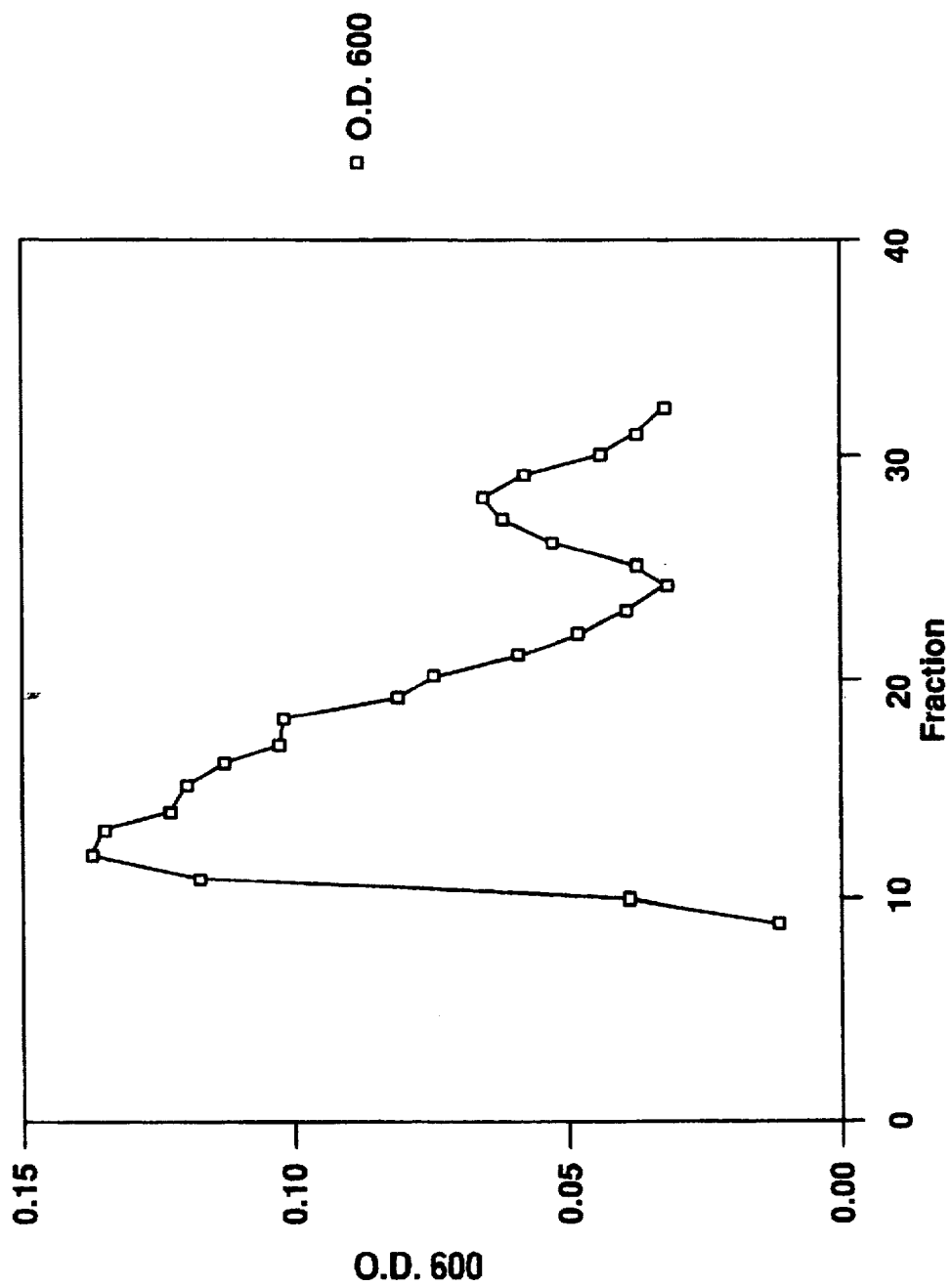
FIG. 3 depicts the elution profile of 20K PEGbv (2 mg/mL bed volume loading) from a ToyoPearl® Butyl 650M HIC column. PEG-containing fractions were detected with Nessler's reagent and turbidity measured at 600 nm.

Run 2 used a ToyoPearl® Butyl 650M HIC column (1.5×11.4 cm). The 650M resin differs from the 650C resin in that the particle size is 40–90 microns rather than 50–150 microns. The column was equilibrated in 2M NaCl and 2 mg/mL bed volume PEGbv was loaded onto the column. The PEGbv was eluted using a 10 column volume linear NaCl gradient (2M NaCl to 0M NaCl) and a flow-rate of 1.5 mL/minute. 3 minute fractions were collected and the elution profile is depicted in FIG. 3. The % yield of 20K PEGbv was then determined using the assay described in Example 3 (see Table 2).

Run 3

Run 3 used a ToyoPearl® Butyl 650M HIC column (3.2×18.0 cm). The column was equilibrated in 2.5M NaCl and 1.8 mg/mL bed volume PEGbv was loaded onto the column. The PEGbv was eluted using a 10 column volume linear NaCl gradient (2M NaCl to 0.5M NaCl) and a flow-rate of 9.6 mL/minute. 2.5 minute fractions were collected. The % yield of 20K PEGbv was then determined using the assay described in Example 3 (see Table 2).

Run 4

Run 4 used a ToyoPearl® Butyl 650M HIC column (1.5×11.5 cm). The column was equilibrated in 5M NaCl and 8 mg/mL bed volume PEGbv was loaded onto the column. The increased bed volume loading was performed in order to more closely approximate running conditions at large scale. And, because of the increased loading, a higher NaCl concentration (5M vs. 2M) was required for complete binding of PEGbv onto the column. The PEGbv was eluted using a 10 column volume linear NaCl gradient (3.5M NaCl to 1M NaCl) and a flow-rate of 2.0 mL/minute. 1.5 minute fractions were collected. The % yield of 20K PEGbv was then determined using the assay described in Example 3 (see Table 2).

Run 5

Figure 4:
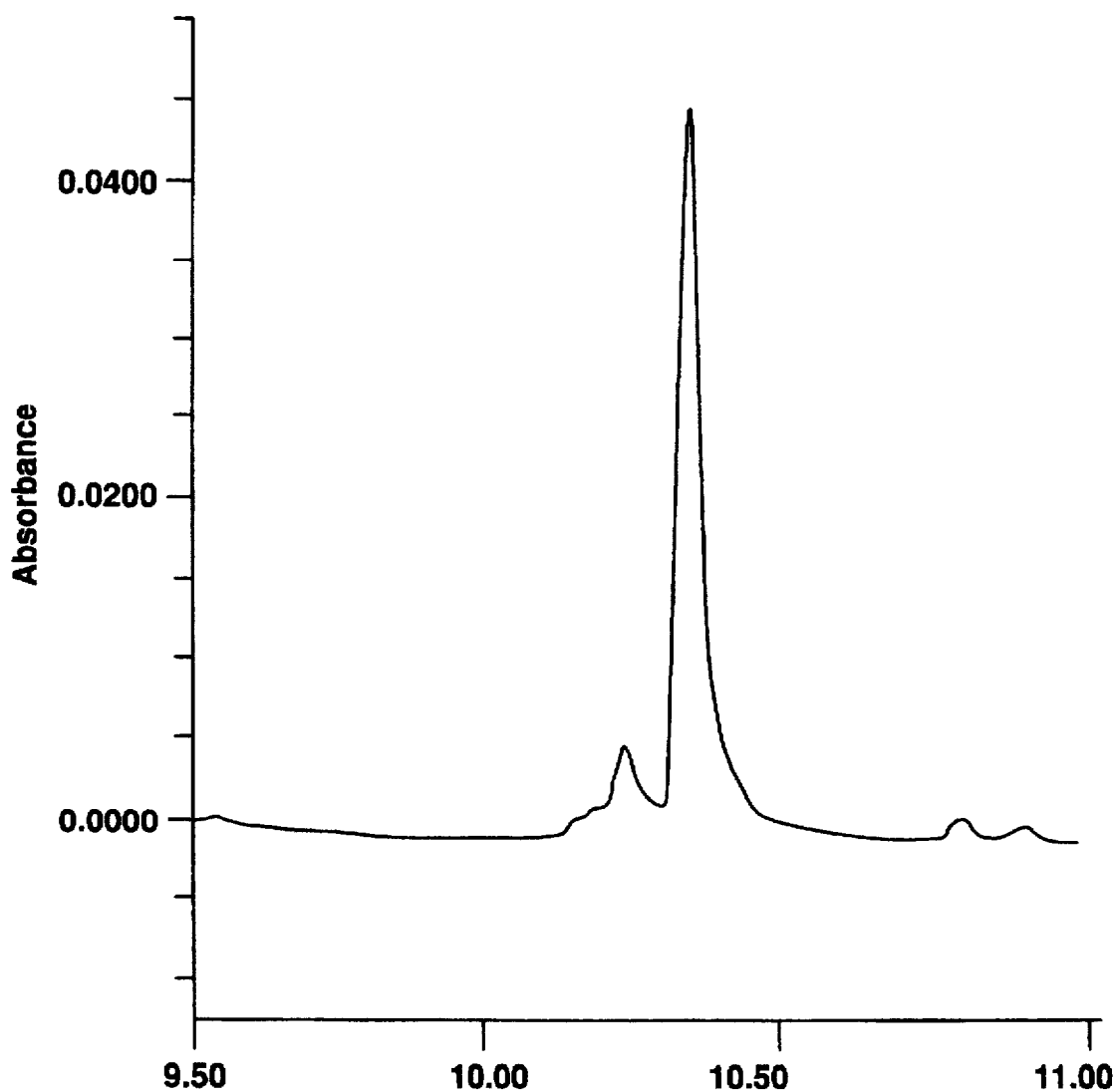
FIG. 4 depicts the elution profile of non-HIC-purified 20K PEGbv from a SEC-HPLC column.
Figure 5:
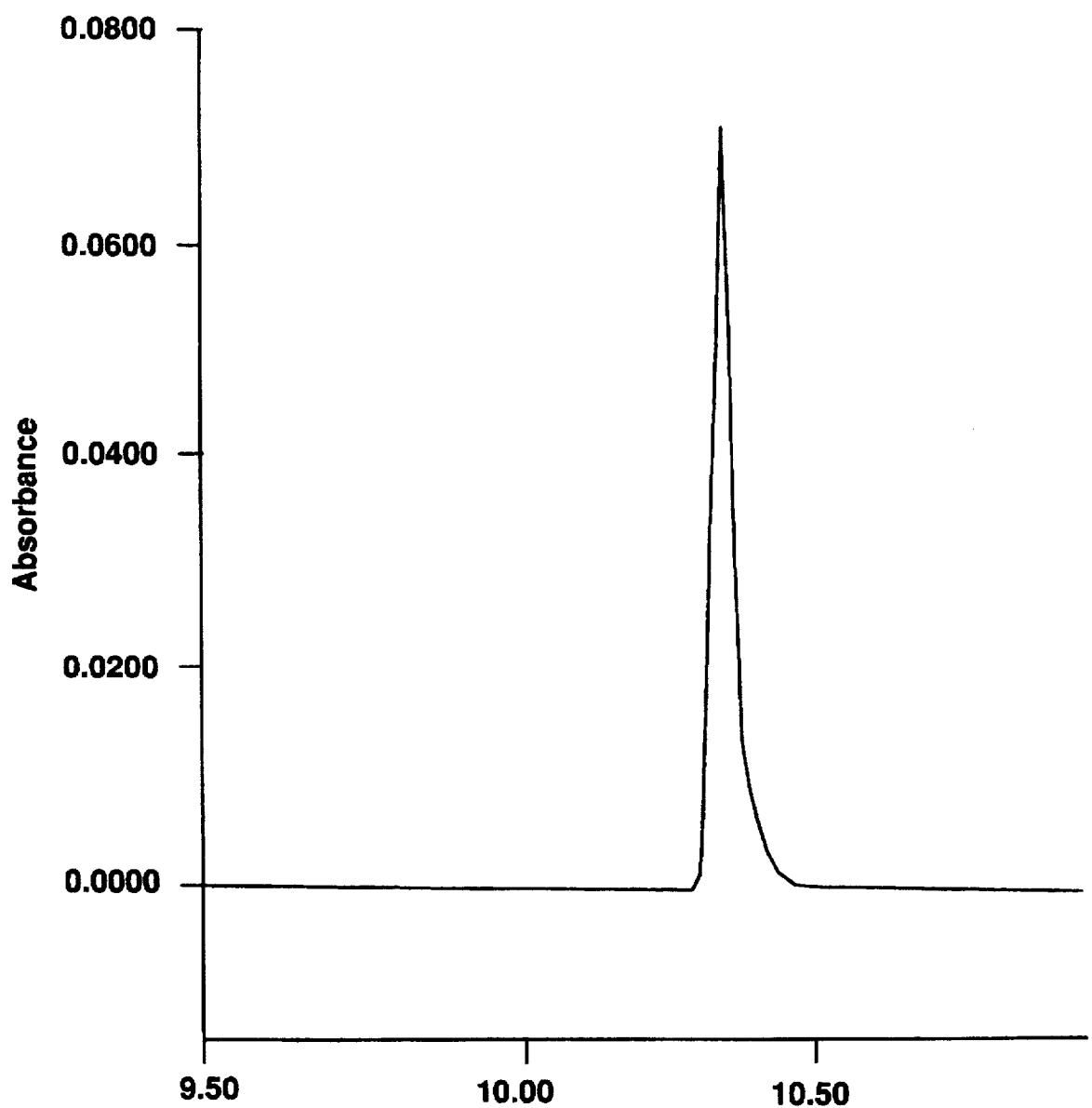
FIG. 5 depicts the elution profile of HIC-purified 20K PEGbv from a SEC-HPLC column. A ToyoPearl® Butyl 650M HIC column (8 mg/mL bed volume loading) was used for the HIC purification.

Run 5 used a ToyoPearl® Butyl 650M HIC column (1.5×11.5 cm). The column was equilibrated in 5M NaCl and 8 mg/mL bed volume PEGbv was loaded onto the column. The PEGbv was eluted using a 15 column volume linear NaCl gradient (2M NaCl to 0.5M NaCl) and a flow-rate of 2.1 mL/minute. Fractions were collected and the elution profile is depicted in FIG. 3. The resolution profile was not as good for this run as that obtained using 2 mg/mL loading; however, SEC HPLC purity obtained from the run was determined and is represented in FIGS. 4 and 5. The FIGS. 4 and 5 data demonstrates that, despite the poorer resolution, adequate removal of the high molecular weight PEGbv was achieved.

Run 6

Run 6 used a ToyoPearl Butyl® 650M HIC column (7.0×14 cm). The column was equilibrated in 4.5M NaCl and 8 mg/mL bed volume PEGbv was loaded onto the column. The PEGbv was eluted using a 17 column volume linear NaCl gradient (3.5M NaCl to 1.0M NaCl) and a flow-rate of 55 mL/minute.

TABLE 2

| Run # | Resin | Load (mg PEGbv/ mL bed volume) | % yield 20K PEGbv |
|---|---|---|---|
| 1 | Phenyl 650S | 2 mg/mL | 75% |
| 2 | Butyl 650M | 2 mg/mL | 73% |
| 3 | Butyl 650M | 1.8 mg/mL | 64% |
| 4 | Butyl 650M | 8 mg/mL | 72% |
| 5 | Butyl 650M | 8 mg/mL | N/D* |
| 6 | Butyl 650M | 8 mg/mL | N/D |

*N/D = Not Determined

As indicated by the data above, the use of linear NaCl gradients in the Phenyl and/or Butyl HIC separations is effective in resolving high molecular weight PEGbv from the 20K PEGbv. Furthermore, a yield of approximately 70%–75% can be obtained using a 2 mg/mL bed volume loading or an 8 mg/mL bed volume loading under appropriate conditions. Finally, the data indicate that, although the resolution profile is not as good for the 8 mg/mL loading runs as compared to the 2 mg/mL loading runs, the 8 mg/mL loading does achieve adequate removal of the high molecular weight PEGbv.

EXAMPLE 5

This example describes the preparation of a biologically-active conjugate (homodumbbell) comprising TNFbp and HIC-purified 20K PEGbv. The overall yield, purity, and biological activity of the conjugate is compared to previously described TNFbp conjugates.

Conjugate Preparation

The TNFbp used in this example was c105 30 kDa TNFbp mutein prepared as described in published PCT Publication No. WO 92/16221, incorporated herein by reference. The 20K PEGbv used in the example was synthesized using the "One-step" procedure as described in Example 1 above. A portion of the synthesized 20K PEGbv was then HIC-purified as described in Example 4, Run 5. Both non-HIC-purified and HIC-purified 20K PEGbv was then used to prepare PEGbv:TNFbp conjugates.

The conjugates were prepared as follows: the c105 30 kDa TNFbp mutein was exposed to a 1.3-fold molar excess of DTT in 20 mM phosphate, pH 7.6, for 5–6 hours at 15° C. in order to remove an extra cysteine attached to c105 during the refolding process. The pH was adjusted to 6.0 and the sample loaded onto a S-Sepharose Fast Flow column (at 4–6 mg/mL bed volume), washed with 3 column volumes of 20 mM phosphate buffer, pH 6.0 (to remove the DTT) and eluted with 20 nM phosphate, 70 mM NaCl, pH 6.0. The reduced c105 30 KDa TNFbp mutein solution was then adjusted to pH 7.4–7.5 and reacted with 0.6–0.7 mg of the HIC-purified or non-HIC-purified 20K PEGbv per mg of TNFbp for 12–18 hours, at ambient temperature.

Conjugate Analysis

PEGylation Assay

Figure 6:
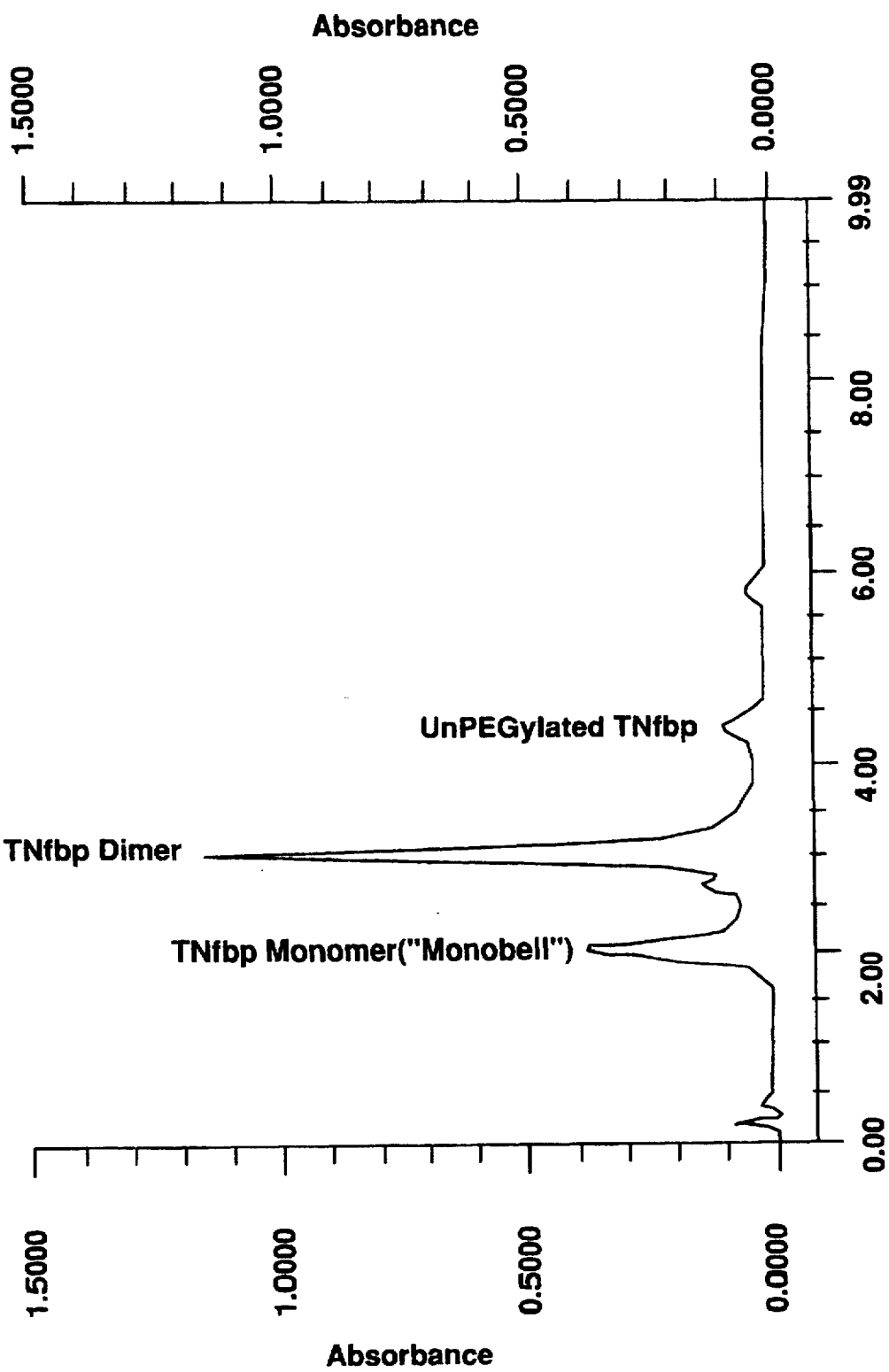
FIG. 6 depicts a typical POROS HS cation-exchange elution profile for a TNFbp PEGylation mixture (the mixture utilized non-HIC-purified 20K PEGbv). The various TNFbp peaks are shown as indicated.

The conversion of TNFbp into 20K PEGbv:TNFbp dumbbell was quantitated using a POROS HS/H 4.6/50 cation exchange HPLC column (Perseptive Biosystems). A 50 μl sample was loaded onto the column and a 10 minute, 20 mM sodium acetate, pH 3.75, 0–1M NaCl gradient used to elute the sample from the column. A representative elution profile for a TNFbp monobell, i.e., PEGbv with TNFbp attached at only one end, TNFbp dumbbell, and an unpegylated TNFbp sample was depicted in FIG. 6. TNFbp monobell eluted first, followed by TNFbp dumbbell and unPEGylated TNFbp.

Results

Figure 7:
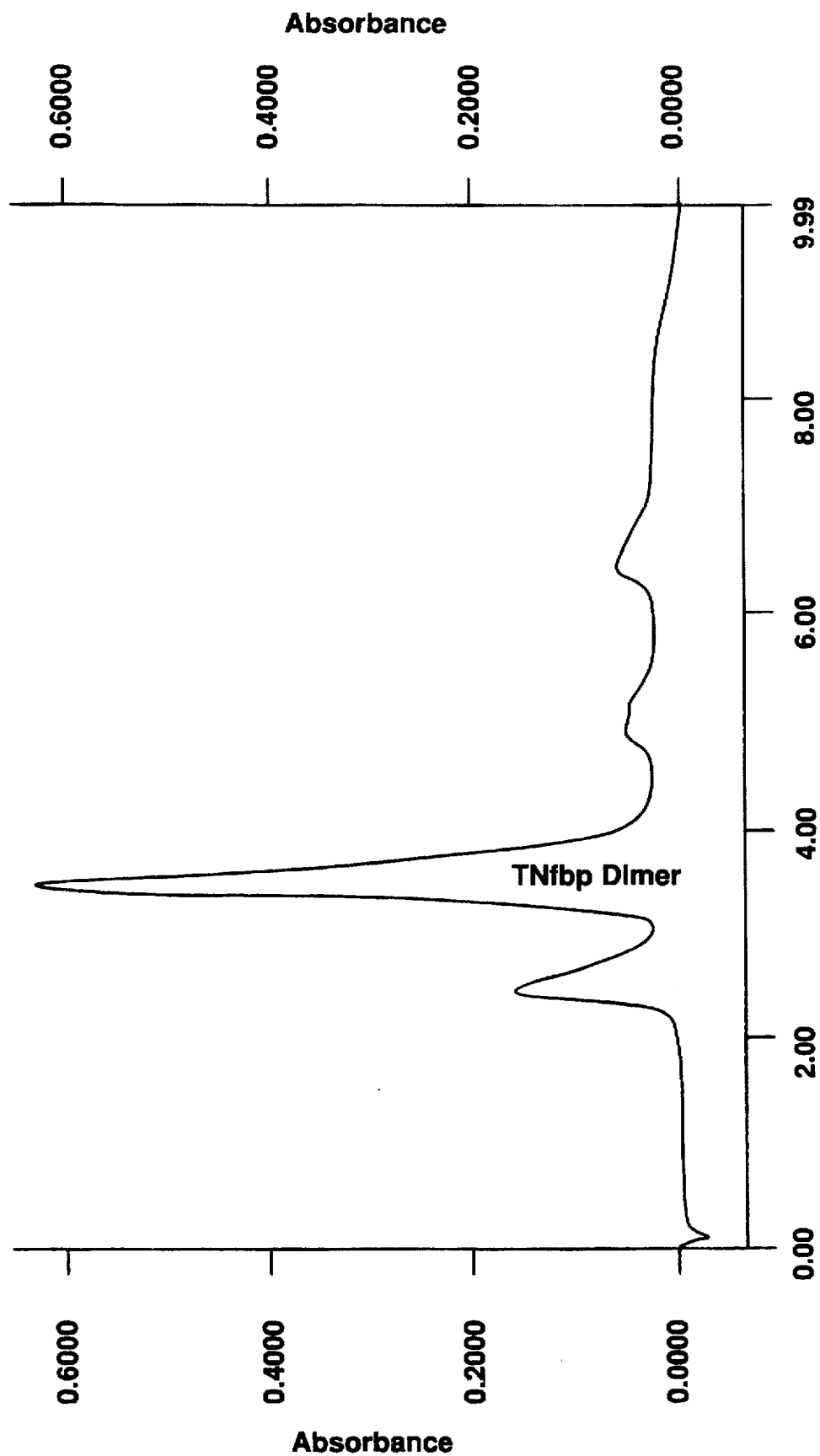
FIG. 7 depicts the POROS HS cation-exchange elution profile for a TNFbp PEGylation mixture. The PEGylation mixture was prepared as described in Example 5 and utilized ToyoPearl® Butyl 650M HIC-purified 20K PEGbv.
Figure 8:
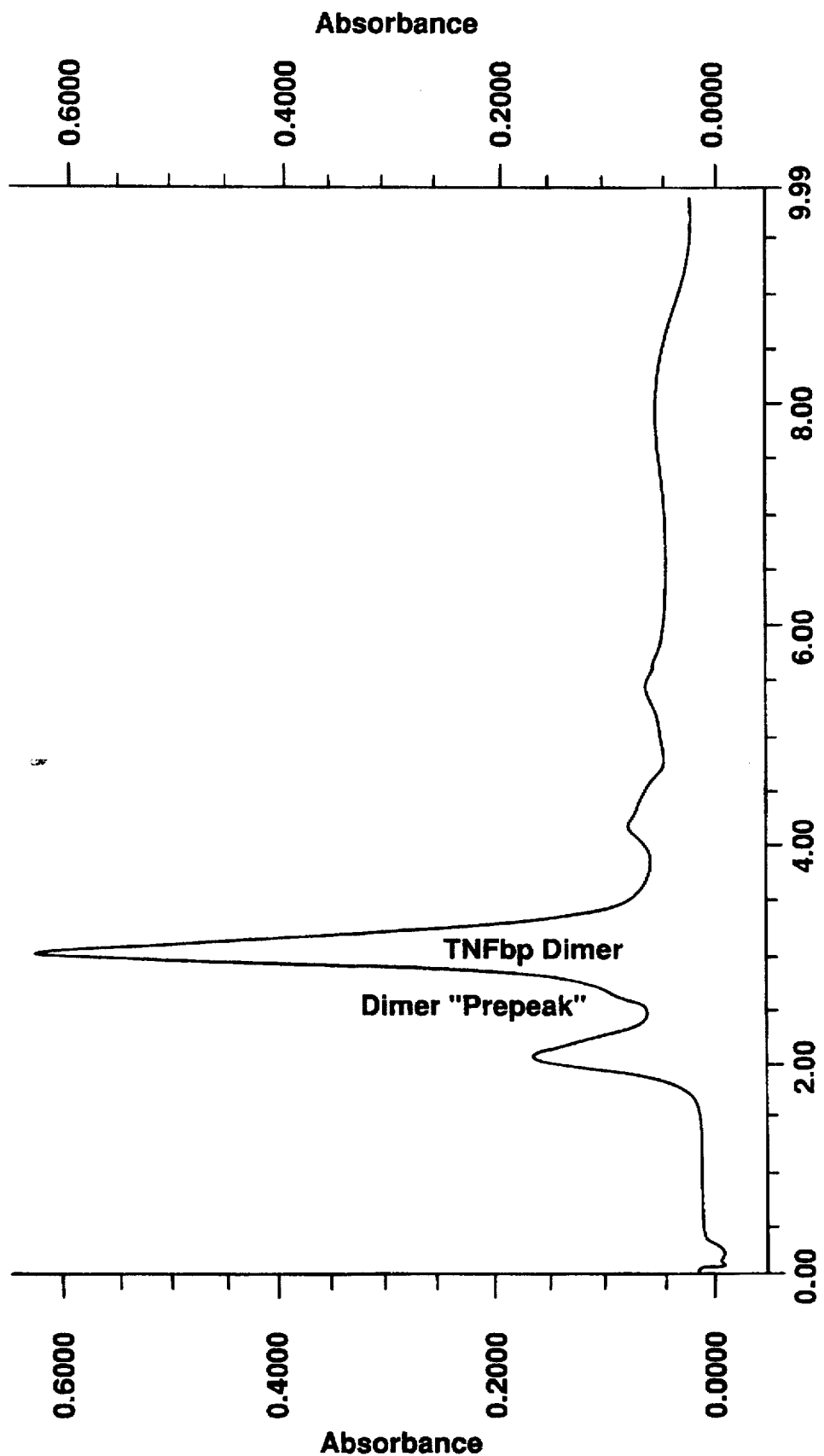
FIG. 8 depicts the POROS HS cation-exchange elution profile for a TNFbp PEGylation mixture. The PEGylation mixture was prepared as described in Example 5 and utilized non-HIC-purified 20K PEGbv.

The percent conversion to TNFbp dumbbell for the HIC-purified material was 66.7%, with no detectable "prepeak" (see FIG. 7). Non-HIC-purified PEGbv from the same lot gave only 52.9% conversion and had 6.7% "prepeak" (see FIG. 8). This distinct "prepeak" is TNFbp dumbbell that is generated with high molecular weight PEGbv impurities.

Figure 9:
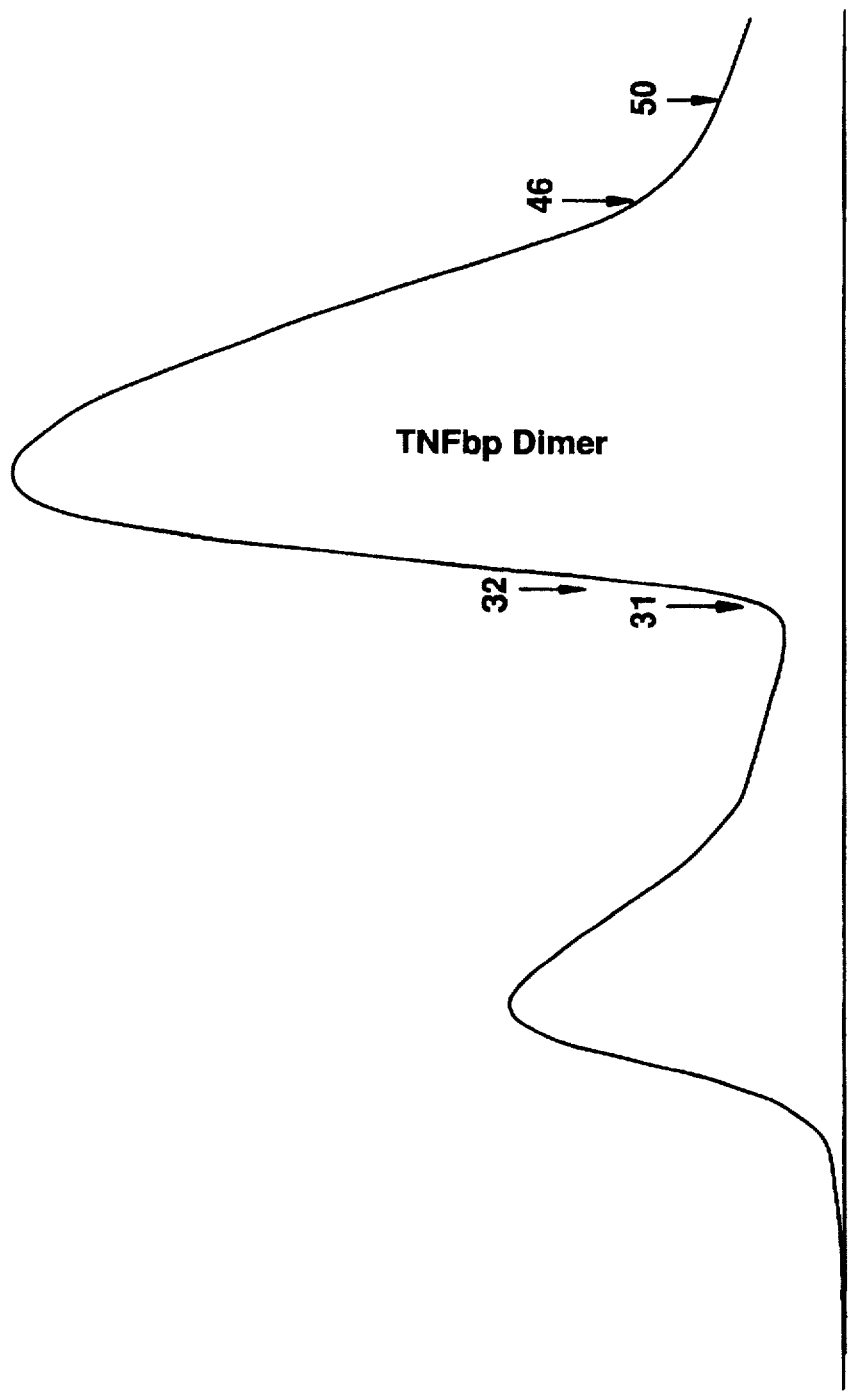
FIG. 9 depicts the elution profile of TNFbp Dimer from a SP-Sepharose HP column. $A_{280}$ absorbance is plotted vs. time. The TNFbp Dimer was prepared using ToyoPearl® Butyl 650M HIC-purified 20K PEGbv.
Figure 10:
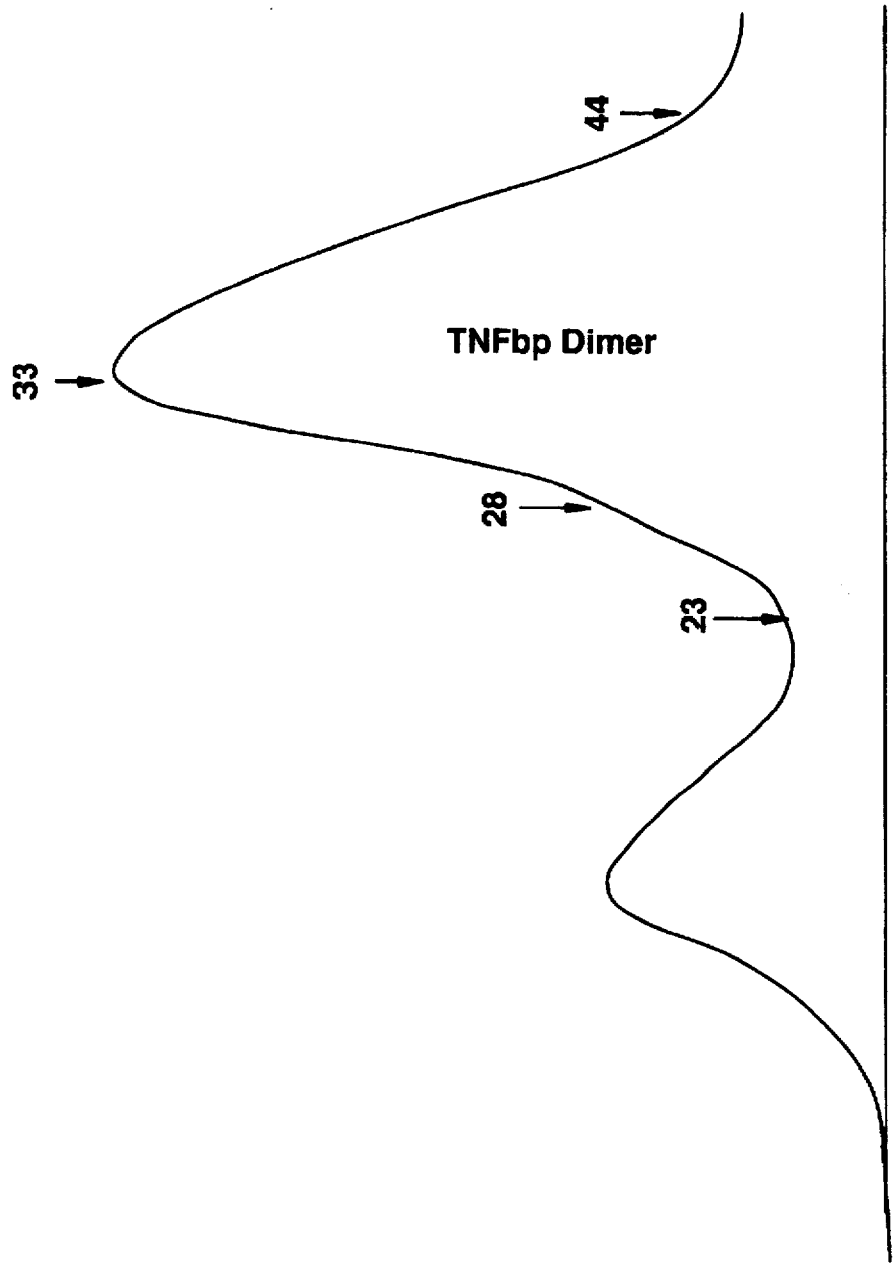
FIG. 10 depicts the elution profile of TNFbp Dimer from a SP-Sepharose HP column. $A_{280}$ absorbance is plotted vs. time. The TNFbp Dimer was prepared using non-HIC-purified 20K PEGbv.

The PEGylation mixtures were then loaded onto 1.5×10 cm SP-Sepharose HP columns (4 mg/mL bed volume) equilibrated in 50 mM sodium phosphate, pH 3.1. After loading, the column was washed with equilibration buffer and then the TNFbp Dimer eluted using 20 column volumes of a 50 mM sodium phosphate, 0.25M NaCl, pH 3.1–50 mM sodium phosphate, 0.5M NaCl, pH 3.1 gradient. The elution profiles are shown in FIGS. 9 and 10. Pooling was done several different ways for each run. Table 3 shows the TNFbp Dimer % yield and % purity for the various pooling criteria used.

TABLE 3

| TNFbp Dimer Sample | Pooled Fractions | % yield 20K PEGbv | % purity 20K PEGbv |
|---|---|---|---|
| HIC-purified PEGbv | 31–36 | 53.70% | 96.90% |
|  | 32–46 | 53.30% | 97.40% |
|  | 31–50 | 58.00% | 97.10% |
| Unpurified PEGbv | 23–44 | 55.30% | 83.50% |
|  | 28–44 | 50.70% | 90.60% |
|  | 33–44 | 35.50% | 97.30% |

The Table 3 data shows a clear benefit of PEGbv HIC purification on subsequent TNFbp Dimer purity and yields. For example, in order to obtain 97% purity with the non-HIC-purified PEGbv, only 37% of the TNFbp Dimer could be recovered on SP-Sepharose HP; whereas as much as 58% could be recovered with the HIC-purified material, i.e., HIC purification of 20K PEGbv can increase the recovery of TNFbp Dimer by as much as 1.5–1.6 fold.

EXAMPLE 6

In this example, the ability of the HIC resin to separate PEGs based on end-group functionality was evaluated.

Figure 11:
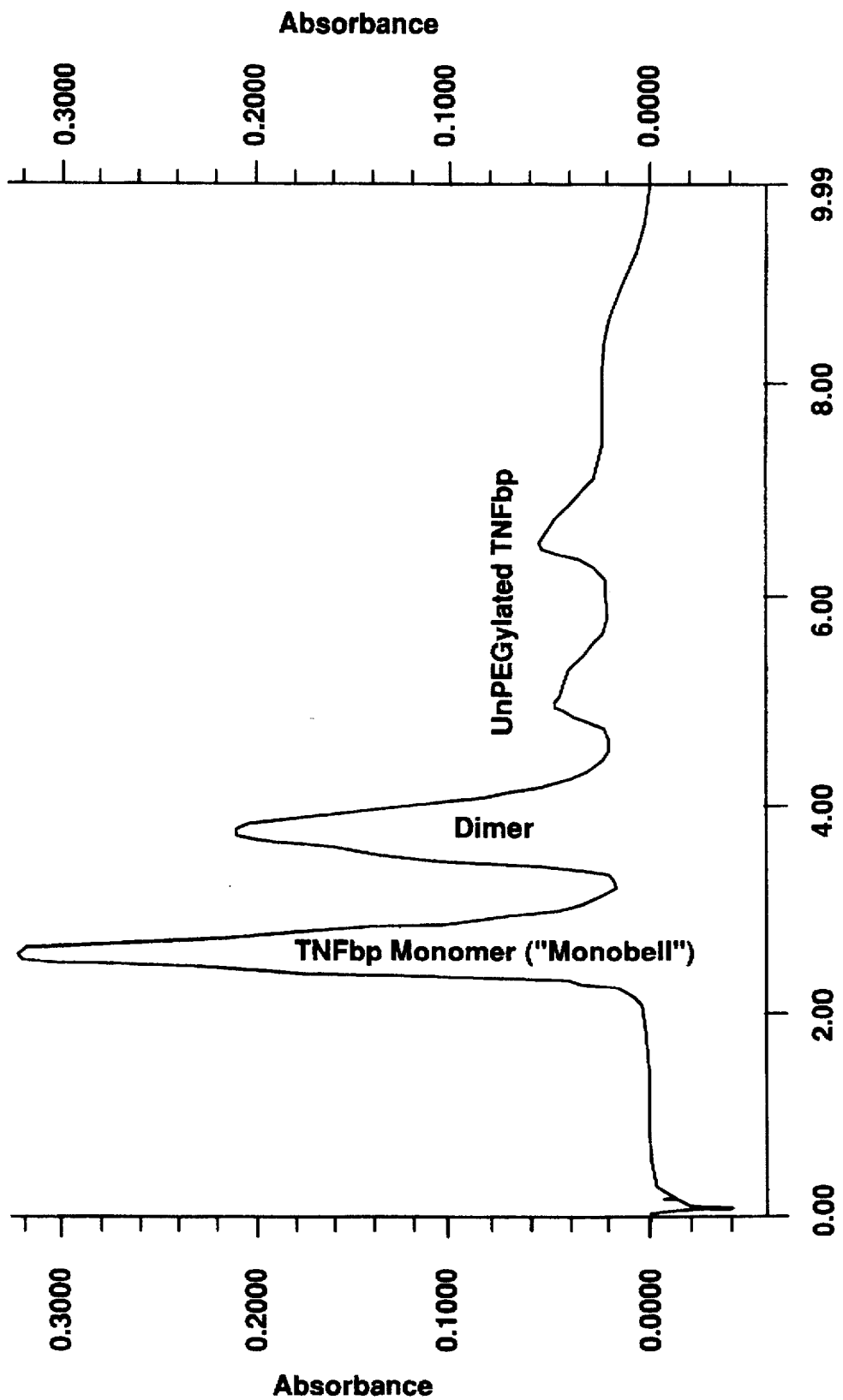
FIG. 11 depicts the POROS HS cation-exchange elution profile for an "early eluting" fraction from a 20K PEGbv ToyoPearl® Butyl 650M HIC purification. The PEGylation mixture was prepared as described in Example 6.

The "early eluting" material from Example 4, Run 3 was tested in the PEGylation assay. The "early eluting" material was those fractions which eluted just in front of the fractions which were pooled to provide the 20K PEGbv. And, as shown in FIG. 11, this material made mostly TNFbp monobell. This indicates that the "early eluting" material contains predominantly PEG 20K mono-vinylsulfone, and demonstrates the ability of the Butyl HIC resin to separate 20K PEGbv based on end-group functionality.

What is claimed is:

1. A process for purifying a polyethylene glycol (PEG), said process comprising:
   (a) applying said PEG to a hydrophobic interaction chromatography (HIC) column, wherein said HIC utilizes polymeric resins wherein a hydrophobic pendant group selected from the group consisting of octyl, butyl, phenyl, and ether is located on the surface of a hydrophilic vinyl copolymer backbone resin; and
   (b) selectively isolating the desired PEG form by utilizing elution conditions which allow for separation of the various PEG forms based on size.

2. A process according to claim 1, said HIC comprising a butyl or phenyl ligand on a methacrylic backbone.

3. A process according to claim 1, said elution condition comprising a reverse linear salt gradient.

4. A process according to claim 1, said polyethylene glycol having a molecular weight of 5 kDa to 100,000 kDa.

5. A process according to claim 1, said polyethylene glycol having at least one active sulfone moiety.

6. A process according to claim 5, wherein said active sulfone moiety is vinyl sulfone.

7. A process according to claim 5, wherein said polyethylene glycol is polyethylene glycol-bis-vinyl sulfone.

8. A process for purifying a polyethylene glycol (PEG), said process comprising:
   (a) applying said PEG to a hydrophobic interaction chromatography (HIC) column, wherein said HIC utilizes polymeric resins wherein a hydrophobic pendant group selected from the group consisting of octyl, butyl, phenyl, and ether is located on the surface of a hydrophilic vinyl copolymer backbone resin; and
   (b) selectively isolating the desired PEG form by utilizing elution conditions which allow for separation of the various PEG forms based on end-group functionality.

9. A process according to claim 8, said HIC comprising a butyl or phenyl ligand on a methacrylic backbone.

10. A process according to claim 8, said elution condition comprising a reverse linear salt gradient.

11. A process according to claim 8, said polyethylene glycol having a molecular weight of 5 kDa to 100,000 kDa.

12. A process according to claim 8, said polyethylene glycol having at least one active sulfone moiety.

13. A process according to claim 12, wherein said active sulfone moiety is vinyl sulfone.

14. A process according to claim 12, wherein said polyethylene glycol is polyethylene glycol-bis-vinyl sulfone.

15. A substantially homogenous polyethylene glycol product produced by the process of claim 1.

16. A product according to claim 15 having a molecular weight ranging from 5 kDA to 100 kDa.

* * * * *

UNITED STATES PATENT AND TRADEMARK OFFICE
CERTIFICATE OF CORRECTION

PATENT NO.   : 5,747,639
DATED        : May 5, 1998
INVENTOR(S)  : James E. Seely It is certified that error appears in the above-identified patent and that said Letters Patent is hereby corrected as shown below:

On the title page, second column, line 10, change "HPL" to -- HPLC --

On the title page, second column, line 13, change "(1992)" to -- (1993) --

Column 6, line 11, change "TiNF" to -- TNF --

Column 6, line 14, after TNF add -- " --

Column 9, line 23, change "chromatoaraphy" to -- chromatography --

Column 11, line 64, change "Kda" to -- kDa --

Signed and Sealed this

Nineteenth Day of October, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO. : 5,747,639　　　　　　　　　　　　　　　　　　　Page 1 of 1
APPLICATION NO. : 08/611918
DATED : May 5, 1998
INVENTOR(S) : Seely It is certified that error appears in the above-identified patent and that said Letters Patent is hereby corrected as shown below:

Column 13, Claim # 4, the term "100,000 kDa" should read --100 kDa--.

Column 14, Claim # 11, the term "100,000 kDa" should read --100 kDa--.

Signed and Sealed this

Twenty-second Day of August, 2006

JON W. DUDAS
*Director of the United States Patent and Trademark Office*